United States Patent
Putnam et al.

(10) Patent No.: US 10,344,243 B2
(45) Date of Patent: Jul. 9, 2019

(54) BIOMIMETIC BOUNDARY LUBRICANTS FOR ARTICULAR CARTILAGE

(71) Applicant: CORNELL UNIVERSITY, Ithaca, NY (US)

(72) Inventors: David Putnam, Ithaca, NY (US); Mingchee Tan, Ithaca, NY (US); Kirk J. Samaroo, Ithaca, NY (US); Lawrence J. Bonassar, Ithaca, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 0 days.

(21) Appl. No.: 14/436,677

(22) PCT Filed: Oct. 18, 2013

(86) PCT No.: PCT/US2013/065762
§ 371 (c)(1),
(2) Date: Apr. 17, 2015

(87) PCT Pub. No.: WO2014/063102
PCT Pub. Date: Apr. 24, 2014

(65) Prior Publication Data
US 2015/0275118 A1 Oct. 1, 2015

Related U.S. Application Data

(60) Provisional application No. 61/716,119, filed on Oct. 19, 2012.

(51) Int. Cl.
| | | |
|---|---|---|
| *C10M 107/28* | (2006.01) | |
| *A61K 31/728* | (2006.01) | |
| *A61K 31/48* | (2006.01) | |
| *A61K 31/795* | (2006.01) | |
| *A61L 27/36* | (2006.01) | |
| *A61K 47/66* | (2017.01) | |
| *A61F 2/30* | (2006.01) | |

(52) U.S. Cl.
CPC ......... *C10M 107/28* (2013.01); *A61K 31/728* (2013.01); *A61K 31/795* (2013.01); *A61K 47/66* (2017.08); *A61L 27/3604* (2013.01); *A61L 27/3695* (2013.01); *A61F 2/30756* (2013.01); *A61F 2002/30673* (2013.01); *A61F 2002/30754* (2013.01); *A61L 2400/06* (2013.01); *A61L 2430/24* (2013.01)

(58) Field of Classification Search
CPC ....... A61F 2002/30673; A61F 2/30756; A61K 31/795; A61K 47/48346; A61L 2400/06; C10M 107/28
See application file for complete search history.

(56) References Cited

U.S. PATENT DOCUMENTS

| | | | | |
|---|---|---|---|---|
| 2003/0087111 | A1* | 5/2003 | Hubbell | A61L 27/34 428/457 |
| 2009/0305352 | A1 | 12/2009 | Dai et al. | |
| 2010/0168850 | A1* | 7/2010 | Vanderbilt | C08F 275/00 623/6.11 |

FOREIGN PATENT DOCUMENTS

| | | | |
|---|---|---|---|
| CN | 101511875 A | 8/2009 | |
| CN | 1723232 A | 1/2016 | |
| EA | 014113 B1 | 10/2010 | |
| EA | 014469 B1 | 12/2010 | |
| RU | 2008 132 767 A | 5/2010 | |
| WO | WO 2004/063250 A1 | 7/2004 | |
| WO | WO 2008/063291 | * 5/2008 | ............ A61K 39/00 |
| WO | WO 2010/135541 | * 11/2010 | ............ A61K 38/16 |
| WO | WO 2010/135541 A2 | 11/2010 | |

OTHER PUBLICATIONS

Schmolke et al. (Phys. Status Solidi A 208, No. 6 1290-1300 (2011).*
Muller et al. (Tribology Letters, vol. 15, No. 4, Nov. 2003 pp. 395-405).*
Hongwei Ma et al. (Adv. Mater. 2004. 16, No. 4, Feb. 17 pp. 338-341).*
Klages, C. et al., "Adsorption of poly(acrylic acid)-graft-poly(ethylene glycol) on polyelectrolyte multilayers", 24th Conference of the European Colloid and Interface Society, (Sep. 5, 2010), 1 page.
Schmolke, H. et al., "Polyelectrolyte multilayer surface functionalization of poly(dimethylsiloxane) (PDMS) for reduction of yeast cell adhesion in microfluidic devices", Biomicrofluids, (Dec. 29, 2010), vol. 4, No. 4, pp. 044113-1-044113-12.
Extended European Search Report dated Mar. 23, 2016 issued in corresponding European Patent Application No. 13846337.7.
Arroll B. et al., "Corticosteroid Injections for Osteoarthritis of the Knee: Meta-Analysis", *BMJ* 328(7444):869 (5 pages) (Mar. 2004).
Chawla K. et al., "Molecular Resurfacing of Cartilage With Proteoglycan 4 (PRG4)", *Acta Biomater.* 6(9):3388-3394 (Sep. 2010).
Das S. et al., "Synergistic Interactions Between Grafted Hyaluronic Acid and Lubricin Provide Enhanced Wear Protection and Lubrication", *Biomacromolecules* 14:1669-1677 (2013).
Elsaid K.A. et al., "The Impact of Forced Joint Exercise on Lubricin Biosynthesis from Articular Cartilage Following ACL Transection and Intra-Articular Lubricin's Effect in Exercised Joints Following ACL Transection", *Osteoarthritis and Cartilage* 20:940-948 (2012).
Ershova O.B. et al., "The Problem of Osteoarthritis, Oral and Local Hondroprotektory", Directory of Outpatient Physician, No. 15, pp. 31-33 (2007), together with an English-language translation.

(Continued)

*Primary Examiner* — Anna R Falkowitz
(74) *Attorney, Agent, or Firm* — Scully Scott Murphy & Presser

(57) ABSTRACT

This invention relates to methods of lubrication for biological tissue, especially joint and cartilage surfaces, and to methods of treating osteoarthritis using high molecular weight, hydrophilic polymer brushes, which mimic the structure and activity of lubricin. These synthetic lubricin analog polymer brushes (termed herein graft brush polymers), include poly(acrylic acid) backbones grafted with polyethylene glycol.

7 Claims, 6 Drawing Sheets

Specification includes a Sequence Listing.

(56) References Cited

OTHER PUBLICATIONS

Farndale R.W. et al., "A Direct Spectrophotometric Microassay for Sulfated Glycosaminoglycans in Cartilage Cultures", *Connective Tissue Research* 9:247-248 (1982).

Flannery C.R. et al., "Prevention of Cartilage Degeneration in a Rat Model of Osteoarthritis by Intraarticular Treatment With Recombinant Lubricin", *Arthritis & Rheumatism* 60(3):840-847 (Mar. 2009).

Gleghorn J.P. et al., "Lubrication Mode Analysis of Articular Cartilage Using Stribeck Surfaces", *Journal of Biomechanics* 41:1910-1918 (2008).

Gleghorn J.P. et al., "Boundary Mode Lubrication of Articular Cartilage by Recombinant Human Lubricin", *Journal of Orthopaedic Research* 27:771-777 (Jun. 2009).

Hartung W., "Aqueous Lubrication of Ceramics by Means of Brush-Forming Graft Copolymers", Doctoral Dissertation ETH No. 18428 (149 pages) (Jun. 2009).

Jay G.D. et al., "Prevention of Cartilage Degeneration and Restoration of Chondroprotection by Lubricin Tribosupplementation in the Rat Following Anterior Cruciate Ligament Transection", *Arthritis & Rheumatism* 62(8):2382-2391 (Aug. 2010).

Jay G.D., "Lubricin and Surfacing of Articular Joints", *Current Opinion in Orhtopaedics* 15:355-359 (2004).

Jay G.D. et al., "Comparison of the Boundary-Lubricating Ability of Bovine Synovial Fluid, Lubricin, and Healon", *J. Biomed Mater Res* 40:414-418 (1998).

Jones A R.C. et al., "Binding and Localization of Recombinant Lubricin to Articular Cartilage Surfaces", *Journal of Orthopaedic Research* 25:283-292 (Mar. 2007).

Kim Y-J et al., "Fluorometric Assay of DNA in Cartilage Explants Using Hoechst 33258", *Analytical Biochemistry* 174:168-176 (1988).

Lowe A.B. et al., "Facile Preparation of Transition Metal Nanoparticles Stabilized by Well-Defined (Co)polymers Synthesized via Aqueous Reversible Addition-Fragmentation Chain Transfer Polymerization", *J. Am. Chem. Soc.* 124(39):11562-11563 (2002).

Mabuchi K. et al., "The Effect of Additive Hyaluronic Acid on Animal Joints With Experimentally Reduced Lubricating Ability", *Journal of Biomedical Materials Research* 28:865-870 (1994).

Müller M.T., "Aqueous Lubrication by Means of Surface-Bound Brush-Like Copolymers", Doctoral Dissertation ETH No. 16030 (188 pages) (2005).

Muller M.T., "The Influence of Molecular Architecture on the Macroscopic Lubrication Properties of the Brush-Like Co-Polyelectrolyte Poly(L-Lysine)-g-Poly(Ethylene Glycol) (PLL-g-PEG) Adsorbed on Oxide Surfaces", *Tribology Letters* 15(4):395-405 (Nov. 2003).

Neuman R.E. et al., "The Determination of Hydroxyproline", *J. Biol. Chem.* 184:299-306 (1950).

Pelet J.M. et al., "Poly(Acrylic Acid) Undergoes Partial Esterification During RAFT Synthesis in Methanol and Interchain Disulfide Bridging Upon NaOH Treatment", *Macromolecular Chemistry and Physics* 213:2536-2540 (2012).

Pelet J.M. et al., "An In-Depth Analysis of Polymer-Analogous Conjugation Using DMTMM", *Bioconjugate Chemistry* 22:329-337 (2011).

Perrino C., "Poly(L-Lysine)-g-Dextran (PLL-g-Dex): Brush-Forming, Biomimetic Carbohydrate Chains that Inhibit Fouling and Promote Lubricity", Doctoral Dissertation ETH No. 18224 (113 pages) (2009).

Pritzker K.P.H. et al., "Osteoarthritis Cartilage Histopathology: Grading and Staging", *OsteoArthritis and Cartilage* 14(1):13-29 (2006).

Schmolke H. et al., "Poly(Acrylic Acid)-Graft-Poly(Ethylene Glycol) Preparation and Adsorption on Polyelectrolyte Multilayers (PEMs) for Custom-Made Antiadhesive Surfaces", *Phys. Status Solidi A* 208(6):1290-1300 (2011).

Scott D.L. et al., "The Long-Term Effects of Non-Steroidal Anti-Inflammatory Drugs in Osteoarthritis of the Knee: A Randomized Placebo-Controlled Trial", *Rheumatology* 39:1095-1101 (2000).

Serra L. et al., "Design of Poly(Ethylene Glycol)-Tethered Copolymers as Novel Mucoadhesive Drug Delivery Systems", *European Journal of Pharmaceutics and Biopharmaceutics* 63:11-18 (2006).

Sinusas K., "Osteoarthritis: Diagnosis and Treatment", *American Family Physician* 85(1):49-56 (Jan. 1, 2012).

Spiller K.L. et al., Hydrogels for the Repair of Articular Cartilage Defects, *Tissue Engineering: Part B* 17(4):281-299 (2011).

Sun Y. et al., "Bioreducible PAA-g-PEG Graft Micelles With High Doxorubicin Loading for Targeted Antitumor Effect Against Mouse Breast Carcinoma", *Biomaterials* 34:6818-6828 (2013).

Swann D.A. et al., "The Molecular Basis of Articular Lubrication", *The Journal of Biological Chemistry* 247(24):8069-8073 (Dec. 25, 1972).

Tadmor R. et al., "Thin Film Rheology and Lubricity of Hyaluronic Acid Solutions at a Normal Physiological Concentration", *J Biomed Mater Res* 64:514-523 (2002).

Van Der Heide E. et al., "Skin Tribology: Science Friction?", *Friction* 1(2):130-142 (2013).

International Search Report dated Jan. 30, 2014 received from Application No. PCT/US2013/065762.

Dedinaite, A. et al., "Biomimetic lubrication" Soft Matter, (2012), vol. 8, pp. 273-284.

Chinese Office Action dated Nov. 2, 2016 received in Chinese Patent Application No. 201380065766.1.

Chinese Office Action dated Sep. 4, 2017 issued in CN 201380065766.1 with English Translation.

\* cited by examiner

A)

$$Coefficient\,of\,Friction(\mu) = \frac{Shear\,Load}{Normal\,Load}$$

B)

SEQUENCE LISTING

<160> NUMBER OF SEQ ID NOS: 5

<210> SEQ ID NO 1
<211> LENGTH: 7
<212> TYPE: PRT

```
<213> ORGANISM: Artificial Sequence
<220> FEATURE:
<223> OTHER INFORMATION: Synthetic Peptide (cartilage binding peptide)

<400> SEQUENCE: 1

Thr Lys Lys Thr Leu Arg Thr
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic Peptide (cartilage binding peptide)

<400> SEQUENCE: 2

Ser Gln Asn Pro Val Gln Pro
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Peptide (cartilage binding peptide)

<400> SEQUENCE: 3

Trp Tyr Arg Gly Arg Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Peptide (cartilage binding peptide)

<400> SEQUENCE: 4

Ser Tyr Ile Arg Ile Ala Asp Thr Asn
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Peptide (cartilage binding peptide)

<400> SEQUENCE: 5

Cys Gln Asp Ser Glu Thr Arg Phe Tyr
1               5
```

BIOMIMETIC BOUNDARY LUBRICANTS FOR ARTICULAR CARTILAGE

CROSS-REFERENCE TO RELATED APPLICATIONS

This application claims priority under 35 U.S.C. § 119(e) to provisional application U.S. Ser. No. 61/716,119, filed Oct. 19, 2012, which is incorporated herein in its entirety.

STATEMENT REGARDING FEDERALLY SPONSORED RESEARCH

This invention was made with government support under Grant No. DMR-0520404, awarded by the National Science Foundation. The government has certain rights in the invention.

INCORPORATION BY REFERENCE OF SEQUENCE LISTING

The Sequence Listing in the ASCII text filed, named as 29399_6095_03_US_Sequence_Listing.txt of 2 KB, created on Apr. 17, 2015, and submitted to the United States Patent and Trademark Office via EFS-Web, is incorporated herein by reference.

FIELD OF THE INVENTION

This invention relates to methods of lubrication for biological tissue, especially joint and cartilage surfaces, and to methods of treating osteoarthritis using high molecular weight, hydrophilic polymer brushes, which mimic the structure and activity of lubricin. These synthetic lubricin analog polymer brushes (termed herein graft brush polymers), include poly(acrylic acid) backbones grafted with polyethylene glycol.

BACKGROUND OF THE DISCLOSURE

Osteoarthritis afflicts over 50 million individuals in the developed world and this number is expected to rise as median age and life expectancy increase. The economic impact of osteoarthritis treatment exceeds $30 billion annually in the United States alone. The financial burden, as well as other factors (i.e., quality of life, loss of labor hours, etc.) incentivizes development of more effective treatments.

Current treatments for osteoarthritis (OA) include non-steroidal anti-inflammatories [Scott et al. (2000) Rheumatol. 39:1095-101], intra-articular corticosteroid injections [Arroll et al. (2004) BMJ 2004; 328:8693], and chondroitin sulfate or glucosamine supplements [Sinusas (2012) Am. Fam. Physician 85:49-56]; however, they have little or no effect on disease progression. A more recent approach to the treatment of OA is the intra-articular injection of the natural synovial fluid glycosaminoglycan, hyaluronic acid (HA) [Mabuchi et al. (1994) J. Biomed. Mat. Res. 28:865-70]. HA increases synovial fluid viscosity (e.g., viscosupplementation) to reduce the coefficient of friction in the hydrodynamic mode of lubrication [Tadmor et al. (2002) J. Biomed. Mat. Res. 61:514-23]. The other predominant lubrication component in synovial fluid is lubricin, a high molecular weight glycoprotein that reduces the coefficient of friction in the boundary mode of lubrication [Swann et al. (1972) J. Biol. Chem. 247:8069-73; Jay et al. (1998) J. Biomed. Mat. Res. 40:414-8; Chawla et al. (2013) Acta Biomat. 6:3388-94]. As the field of articular cartilage lubrication matures, it appears that both the hydrodynamic and boundary modes of lubrication are needed to prevent disease progression in weight-bearing joints such as the knee [Das et al. (2013) Biomacromol. 14:1669-77].

In damaged cartilage, chondrocyte production of lubricin is compromised and boundary mode lubrication is reduced [Elsaid et al. (2012) Osteoarthritis Cartilage 20:940-948]. Intra-articular injection of supplemental lubricin, as well as the truncated recombinant lubricin construct LUB:1, slows progression of OA in rat models of disease [Jay et al. (2010) Arthritis Rheum. 62:2382-91; Flannery et al. (2009) Arthritis Rheum. 60:840-7]. However, to date, the large-scale recombinant manufacture of both lubricin and LUB:1 remains challenging owing to multiple amino acid repeats in the protein core, as well as the high degree of glycosylation [Jay (2004) Curr. Opin. Orthop. 15:355-359; Jones et al. (2007) J. Orthop. Res. 25:283-292].

Nature's natural lubricants, such as proteoglycan aggregates and mucins (e.g., lubricin) keep natural surfaces hydrophilic. However, to date, the large-scale recombinant manufacture of both lubricin and LUB:1 remains challenging owing to multiple amino acid repeats in the protein core, as well as the high degree of glycosylation [Jay (2004) Curr. Opin. Orthop. 15:355-359; Jones et al. (2007) J. Orthop. Res. 25:283-292]. Consequently a biomimetic for lubricin and LUB:1 capable of providing boundary lubrication is needed.

Lubricating graft another polymers are known in the art but none of these brush copolymers reported as boundary lubricants for articular joints. For example, Müller describes poly(L-lysine)-graft-poly(ethylene glycol) (pLL-g-PEG), a polycationic polymer capable of adsorbing to and lubricating negatively-charged surfaces [Müller (2009) "Aqueous Lubrication by Means of Surface-Bound Brush-Like Copolymers" Doctoral Dissertation ETH No. 16030]. Perrino (2009) reports to pLL-g-dextran as another brush-forming polymer that promotes lubricity of negatively charged surfaces [Perrino (2009) Poly(L-lysine)-g-dextran (pLL-g-dex): Brush-forming, Biomimetic Carbohydrate Chains that Inhibit Fouling and Promote Lubricity" Doctoral Dissertation ETH No. 18224]. Spiller reviews the use of hydrogels for repairing cartilage defects, including natural polymers (e.g., alginate, collagen, fibrin, and hyaluronan) and synthetic polymers (e.g., PVA, PEG and modified PEGs) but does not include any hydrogels that are graft brush copolymers [Spiller et al. (2011) Tissue Eng. 17:281-299].

A poly(acrylic acid)-graft-poly(ethylene glycol) (pAA-g-PEG) was investigated to determine the frictional forced during a sliding interactions between a silicone skin coated with a PAA-g-PEG polymer and artificial grass in the presence and absence of water. Under dry conditions, the coefficient of friction is greater than 1 and under wet conditions, the value is below 0.01 at low sliding velocities [Van der Heide et al. (2009) Friction 1:130-142].

Hartung describes the lubrication of ceramics using brush-forming graft copolymers, including poly(allylamine)-g-PEG and pAA-g-PEG copolymers. These pAA-g-PEG copolymers lowered the coefficient of fraction for sapphire matched tribopairs but not for $ZrO_2$ matched tribopairs. In that study, the pAA-g-PEG polymers had a moderately long backbone (15 kDa), a graft ratio of 3-6 and 5 kDa PEG side chains [Hartung (2009) "Aqueous Lubrication of Ceramics by means of Brush-forming Graft Copolymers" Doctoral Dissertation ETH No. 18428]. Doménech (2006) reports pAA-g-PEG graft copolymers as mucoadhesive delivery systems using 1 kDa and 2 kDa PEG side chains (at varying ratios) [Doménech et al. (2006) Eur. J.

Pharm. Biopharm. 63:11-8]. Sun reported the use of pAA-g-PEG micelles to encapsulate and deliver an anti-cancer drug [Sun et al. (2013) Biomaterials 34:6818-28].

SUMMARY OF THE INVENTION

In one aspect, the present invention provides methods for imparting a suitable level of lubricity to a biological tissue which comprises contacting the biological tissue with an sufficient amount of a composition to impart suitable lubricity. That composition comprises a biological mimetic (biomimetic) for lubricin or LUB1. In certain embodiments, the graft brush copolymer is a poly(acrylic acid)-graft-poly(ethylene glycol) copolymer (abbreviated herein as pAA-g-PEG) or a pAA backbone grafted with other brush segments (e.g., polysaccharides, polypropylene oxide and the like) as described herein. In particular embodiments, the graft brush copolymer is (i) a polyanionic backbone having a polydispersity index ranging from 1.0 to about 1.5 and a molecular weight ranging from about 50 kDa to about 200 kDa, (ii) brush segments having a molecular weight ranging from about 1 kDa to about 20 kDa, and (iii) one or more functionalizable terminal groups. Preferred polymers have a hydrodynamic size of at least about 80 nm, and can range up to 100-120 nm as well as approximate the hydrodynamic diameter of lubricin.

In another aspect, the instant invention relates to a method for treating osteoarthritis which comprises a therapeutically-effective amount of a graft brush polymer administering to an arthritic joint or injured joint of patient, wherein the graft brush copolymer is a pAA-g-PEG, a pAA backbone grafted with other brush segments (e.g., polysaccharides, polypropylene oxide and the like) as described herein or is (i) a polyanionic backbone having a polydispersity index ranging from 1.0 to about 1.5 and a molecular weight ranging from about 50 kDa to about 200 kDa, (ii) brush segments having a molecular weight ranging from about 1 kDa to about 20 kDa, and (iii) one or more functionalizable terminal groups. Preferred polymers have a hydrodynamic size of at least about 80 nm, and can range upto 100-120 nm as well as approximate the hydrodynamic diameter of lubricin.

A still further aspect of the invention is directed a graft brush polymer comprising (i) a polyanionic backbone having a polydispersity index ranging from 1.0 to about 1.5 and a molecular weight ranging from about 50 kDa to about 200 kDa, (ii) brush segments having a molecular weight ranging from about 1 kDa to about 20 kDa, and (iii) one or more terminal groups. Preferably, for these polymers of the invention, the polyanionic backbone is pAA, the brush segment is PEG and the terminal group is a thiol, optionally bound with a cartilage binding agent. The invention further provides pharmaceutical compositions comprising the graft brush copolymer of the invention and a pharmaceutically-acceptable carrier.

DETAILED DESCRIPTION OF THE INVENTION

Figure 1:
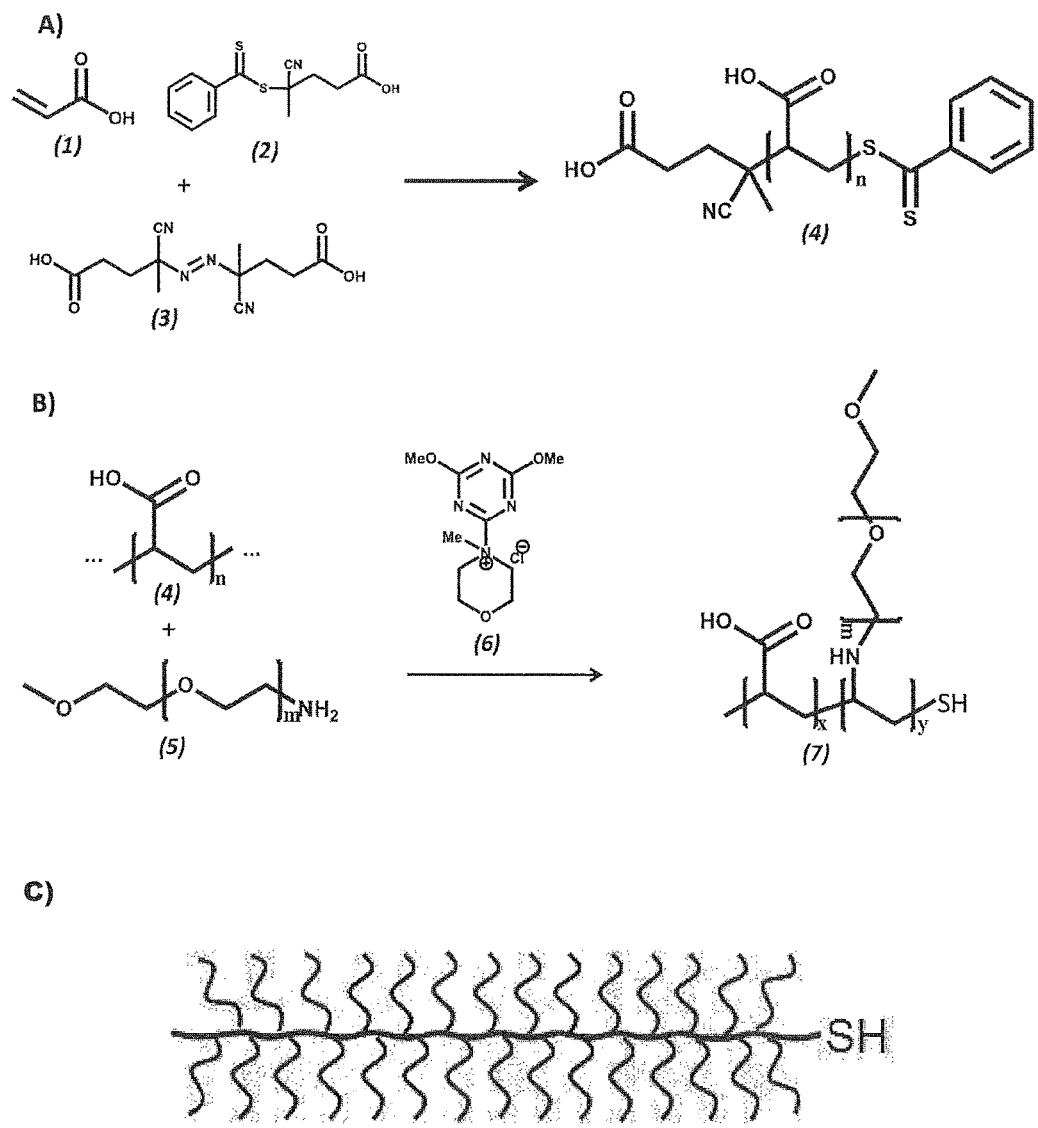
FIG. 1A depicts the RAFT polymerization scheme for acrylic acid (1) using CPA-DB (2) as CTA, and A-CPA (3) as initiator to produce polyacrylic acid (4).
FIG. 1B shows the reaction scheme for conjugation of Methoxy-PEG-amine (5) to polyacrylic acid (4) using carboxylic activating agent DMTMM (6) to yield the statistical graft copolymer (7). The end group is cleaved into —SH in presence of —NH$_2$ groups.
FIG. 1C depicts molecular architecture of the synthetic lubricin mimetic in cartoon format.

The present invention is directed to methods for imparting lubricity to a biological tissue, particularly to joints and cartilage using biomimetic, graft brush copolymers. In accordance with this method, biological tissue is contacted with a composition that comprises a graft brush copolymer that imparts suitable lubricity to surfaces of biological tissue. In certain embodiments, the graft brush copolymer is a poly(acrylic acid)-graft-poly(ethylene glycol) copolymer (abbreviated herein as pAA-g-PEG) or a pAA backbone grafted with other brush segments (e.g., polysaccharides, polypropylene oxide and the like) as described herein. In certain embodiments, the graft brush copolymer comprises (i) a polyanionic backbone having a polydispersity index ranging from 1.0 to about 1.5 and a molecular weight ranging from about 50 kDa to about 200 kDa, (ii) brush segments having a molecular weight ranging from about 1 kDa to about 20 kDa, and (iii) one or more functionalizable terminal groups.

In some embodiments of the present methods, the graft brush copolymer has a polyacrylic acid backbone (pAA) grafted to polyethylene glycol (PEG) brush segments, where the pAA backbone has a size of at least 50 kDa with PEG brush segments of at least 1 kDa, a pAA has a size of at least 60 kDa with PEG brush segments of at least 2 kDa, the pAA backbone has a size of at least 100 kDa with PEG brush segments of at least 5 kDa, the pAA backbone has a size of at least 140 kDa with PEG brush segments at least 10 kDa, and all permutations thereof. Preferred polymers have a hydrodynamic size of at least about 80 nm, and can range up to about 100-120 nm as well as approximate the hydrodynamic diameter of lubricin.

Other brush segments can be used with the pAA backbone, including polysaccharides (e.g., dextran and the like) or polyalcohols (e.g., polyvinyl alcohol (PVA) and the like).

Biological tissues can be contacted by injecting, infusing, implanting, spraying or coating a graft copolymer into, onto or surrounding the tissue or space to be lubricated. In general, contacting a biological tissue means that the graft brush polymer is delivered to the tissue in any manner that leads to coating of the surface or bathing of the tissue with the copolymer. In certain embodiments the tissue is contacted by injection or infusion of the composition into a joint space biological tissue—leading to a coating of cartilage and/or the meniscus found in that joint space. Moreover, the volumes used are determined by the type of tissue being contacted, whether a space is being filled, a surface being coated and so on.

In particular embodiments, the biological tissue is a joint or cartilage, and preferably an injured or arthritic joint and/or cartilage. In preferred embodiments, the joint is a weight bearing joint such as a hip, knee or ankle joint. Many different joints can be need lubricity, including the shoulder, elbow, wrist, hand, finger and toe joints.

Other biological tissues can be lubricated for treatment of a variety of conditions, including but not limited to, dry eye syndrome, dry nose, post-menopausal vaginal dryness, carpal tunnel syndrome and more. Those of skill in the art can determine the appropriate delivery route and method for contacting a particular biological tissue. For example, for dry eyes, contacting may be by instilling drops, for dry nose, contacting may be by nasal spray, for carpal tunnel syndrome contacting may be by injecting near or around the inflamed tendon and capsule, and for post-menopausal dry vagina, a pill, troche or suppository can be placed in or implanted in the vagina. Hence, this method can be used to achieve boundary mode lubrication with any biological tissue.

Another aspect of the invention is directed to methods of treating osteoarthritis using the graft brush polymers described herein. In accordance with these methods, a therapeutically-effective amount of a graft brush polymer is administered to an arthritic joint or an injured joint of a patient. The graft brush polymers which are administered can be a pAA-g-PEG copolymer of varying molecular weight with the pAA backbone molecular weight ranging from at least about 50 kDa to about 200 kDa and the PEG brushes ranging from at least about 1 to about 20 kDa in size. In some embodiments the graft brush copolymer comprises (i) a polyanionic backbone having a polydispersity index ranging from 1.0 to about 1.5 and a molecular weight ranging from about 50 kDa to about 200 kDa, (ii) brush segments having a molecular weight ranging from about 1 kDa to about 20 kDa, and (iii) one or more functionalizable terminal groups.

In some embodiments of the present methods, the polyanionic back bone of the graft brush copolymer is pAA having a molecular weight selected from the group consisting of about 50 kDa, about 75 kDa, about 100 kDa, about 125 kDa and about 150 kDa. The preferred brush segments for these polymers are PEG or dextran, and more preferably, PEG. The molecular weights of the brush segments range in size of from about 1 kDa to about 20 kDa, and for PEG are preferably, about 1 kDa, about 2 kDa, about 5 kDa or about 10 kDa. Preferred polymers have a hydrodynamic size of at least about 80 nm, and can range up to about 100-120 nm as well as approximate the hydrodynamic diameter of lubricin.

The functionalizable terminal group is preferably a thiol moiety. The thiol can be conjugated to a cartilage binding agent, a hydrophobic alkane chain, cholesterol or other agent, including but not limited to, one or more of the cartilage-binding peptides of TKKTLRT, SQNPVQP, WYRGRL, SYIRIADTN or CQDSETRFY (SEQ ID. NOs: 1-5, respectively).

The graft brush copolymer can be injected or infused into the arthritic joint to treat osteoarthritis or an injured joint to prevent osteoarthritis. As such the copolymer provides boundary lubrication. Additionally, the method can comprise simultaneously or sequentially administering hyaluronic acid, synovial fluid, glycosaminoglycan or other agent to provide hydrodynamic lubrication to the joint to further the halt disease progression. These agents can also be administered by injection or infusion.

In preferred embodiments, the arthritic joint is a weight bearing joint such as an hip, knee or ankle joint. Many different joints can be affected by osteoarthritis and the method is contemplated for use with such more than the aforementioned weight bearing joints, including but not limited to, the joints of the shoulder, elbow, wrist, hand, finger and toes. It is within the skill in the art to vary the dose, injection frequency, treatment duration and endpoint for each individual joint As used herein, "treatment" refers to clinical intervention in an attempt to alter the disease course of the individual or cell being treated, and can be performed either for prophylaxis or during the course of clinical disease. Therapeutic effects of treatment include without limitation, preventing occurrence or recurrence of disease, alleviation of symptoms, diminishment of any direct or indirect pathological consequences of the disease, decreasing the rate of disease progression, amelioration or palliation of the disease state, and remission or improved prognosis. For example, treatment of osteoarthritis may result in reduction of symptoms, improved mobility, less joint pain and overall inhibition of disease progression, or prophylaxis in the case of an injured joint.

As used herein, the terms "therapeutically-effective amount" and "effective amount" are used interchangeably to refer to an amount of a composition of the invention that is sufficient to result in the prevention of the development, recurrence, or onset of osteoarthritis or one or more symptoms thereof, to enhance or improve the prophylactic effect(s) of another therapy, reduce the severity and duration of osteoarthritis, ameliorate one or more symptoms of osteoarthritis, prevent the advancement of osteoarthritis, cause regression of osteoarthritis, and/or enhance or improve the therapeutic effect(s) of additional osteoarthritis treatment(s). Similarly, the therapeutically-effective amount is similarly defined for treatment of other diseases or conditions contemplated herein.

A therapeutically-effective amount can be administered to a patient in one or more doses sufficient to palliate, ameliorate, stabilize, reverse or slow the progression of the disease, or otherwise reduce the pathological consequences of the disease, or reduce the symptoms of the disease. The amelioration or reduction need not be permanent, but may be for a period of time ranging from at least one hour, at least one day, or at least one week or more. The effective amount is generally determined by the physician on a case-by-case basis and is within the skill of one in the art. Several factors are typically taken into account when determining an appropriate dosage to achieve an effective amount. These factors include age, sex and weight of the patient, the condition being treated, the severity of the condition, as well as the route of administration, dosage form and regimen and the desired result.

In certain embodiments of the invention, the therapeutically effective amount is an amount that is effective to treat osteoarthritis, achieves pain relief over a period of time, to improve joint movement and flexibility, to reduce friction in the joint or other accepted osteoarthritic measure of improvement.

Hyaluronic acid (HA) is a polysaccharide that is the natural hydrodynamic mode lubricant (fast speed and light normal load) in the knee. It is used clinically as an intraarticular injection to reduce the coefficient of friction on knee articular cartilage in the hydrodynamic mode. Lubricin is a proteoglycan that is the natural boundary mode lubricant (slow and heavy normal load) in the knee. It is not used clinically because its repeating amino acid backbone sequence and extensive glycosylation makes its manufacture challenging. Hence the present biomimetics are provided as boundary mode lubricants.

The results with the method of this invention provide boundary mode lubrication as a complement to, or alternative to, hydrodynamic mode lubrication treatments for OA. For example, weight bearing knees experience a full range of frictional forces. The boundary and hydrodynamic lubricants of lubricin and HA, respectively, work synergistically to provide enhanced lubrication and wear protection than by themselves alone [Das (2013)]. Likewise the copolymers used in this method can work synergistically with HA, the hydrodynamic lubricant, to alter OA disease progression. HA and other hydrodynamic mode lubricants contemplated for use in the present invention are known to those of skill in the art and can be combined for use as known in the art.

Another aspect of the invention provides graft brush copolymers comprising (i) a polyanionic backbone having a polydispersity index (PDI) ranging from 1.0 to about 1.5 and a molecular weight ranging from about 50 kDa to about 200 kDa, (ii) brush segments having a molecular weight ranging from about 1 kDa to about 20 kDa, and (iii) one or more functionalizable terminal groups. The copolymers of the present invention may provide an advantage in therapeutic use.

In some embodiments, these graft brush copolymers of the invention have a polyanionic backbone composed of polyacrylic acid. The polyanionic backbone polymers are biocompatible and also include, but are not limited to, polyglutamic acid, polyaspartic acid, polysaccharides and other biocompatible polyanions.

For pAA backbones, the molecular weights range from about 50 kDa to about 200 kDa and include about 50 kDa, about 75 kDa, about 100 kDa, about 125 kDa and about 150 kDa. The PDI ranges from 1.0 to 1.5 and preferably is equal to or less than 1.35. PDIs in this range are achieved by synthesizing the backbones using RAFT synthesis techniques as described in the Examples.

The brush segments, of the present copolymers can be PEG, polypropylene glycol (PPG), a polysaccharide such as dextran or cellulose or a polyalcohol such as polyvinyl alcohol. The molecular weight of the brush segments range from about 1 kDa to about 20 k DA and include about 1 kDa, about 2 kDa, about 5 kDa or about 10 kDa. Preferred brush segments are PEG.

In a preferred embodiment, the overall molecular weight and size of the graft brush copolymers of the invention approach that of lubricin and can be achieved by appropriate variation of the polyanionic backbone and brush segments in the foregoing size ranges. Similarly, the polymers can a hydrodynamic size of at least about 80 nm, and can range up to about 100-120 nm as well as approximate the hydrodynamic diameter of lubricin.

The graft brush copolymers can have one or more functionalizable terminal groups. Such groups include but are not limited to a thiol group, an amine group or other reactive end group. The groups can be located on either one or both ends. The terminal group is useful for binding the copolymer to a surface (with binding generally being orthogonal to that surface), including but not limited to, material and biological surfaces (e,g., glass, metal, gold-coated glass slides) or can be used to for attach one or more functional groups such as a cartilage binding domain—which in turn bind to a surface and orient the copolymer generally orthogonal to that surface. Examples of cartilage binding domain include such peptide moieties as TKKTLRT, SQNPVQP, WYRGRL, SYIRIADTN and CQDSETRFY (SEQ ID NOs: 1-5, respectively), as well as hydrophobic alkane chains (having for example from 6 to 12 carbon atoms), a cholesterol or other sterol moiety, any other binding domain or moiety useful for binding the graft brush copolymer to a biological tissue or material surface. Conjugation chemistry for attaching cartilage binding domains, hydrophobic alkane chains, sterols or other agents are known to those of skill in the art.

For the copolymers of the invention, fictional forces drop with increased PEG chain length and the grafting ratio plays a role, as higher chain density leads to better brushes because chains must lengthen to be accommodated, presumably allowing more water and better lubrication. Frictional coefficients are measured using a tribometer, which evaluates surface lubrication by linear oscillation of a sample at variable speeds (generally, 0.1, 0.3, 1, 3, and 10 mm/s) and variable compressive normal stresses (generally 250 to 300 kPa).

A still further aspect of the invention is directed to a pharmaceutical composition comprising a graft brush copolymer of the invention and a pharmaceutically-acceptable carrier.

Pharmaceutical compositions of the invention can be prepared for intraarticular, intranasal, intravaginal, ocular or other delivery in the form of injectable sterile solutions, suspensions or other convenient preparation (such as a pill, troche, cream, suppository and the like). In addition to the active ingredient, the pharmaceutical compositions of the invention may further comprise, for example, pharmaceutically acceptable additives, excipients, carriers, and the like, that may improve, for example, manufacturability, administration, uptake, and so on.

The term "excipients" refer to pharmacologically inert ingredients that are not active in the body. See HANDBOOK OF PHARMACEUTICAL EXCIPIENTS (Am. Pharm. Ass'n 1986). One of ordinary skill in the art will recognize that many different excipients can be used in formulations according to the present invention and the list provided herein is not exhaustive.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The dosage levels of the graft brush copolymers in the pharmaceutical compositions of the invention may be varied so as to obtain an amount which is effective to achieve the desired therapeutic response for a particular treatment, subject, composition, and mode of administration without being toxic to the subject. The selected dosage level will depend upon a variety of factors including disease being treated, the route of administration, the time of administration, the rate of excretion of the particular compound being employed, the duration of the treatment, other drugs, compounds and/or materials used in combination with the particular compounds employed, the age, sex, weight, condition, general health and prior medical history of the subject being treated, and like factors well known in the medical arts. Multiple administrations of the pharmaceutical compositions is contemplated, including daily, weekly, monthly or bimonthly administration. Preferred dosage levels range from about 0.1-10 mg/mL in injection volumes of 0.1-10 mL (for humans, less for rodents), or an equivalent, and preferably are about 1-5 mg/mL in an injection volume of 0.1 to 3 mL.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. All references patents, patent applications or other documents cited are herein incorporated by reference in their entirety.

EXAMPLES

Materials

Acrylic acid (AA, 99.5%) stabilized with 200 ppm 4-methoxyphenol, methanol (99.8%) and sodium borate buffer were obtained from VWR (Radnor, Pa., USA). 4,4'-azobis(4-cyanopentanoic acid) (A-CPA) and 4-cyano-4-(phenylcarbonothioylthio)pentanoic acid (CPA-DB) (>97% HPLC) was obtained from Sigma-Aldrich (St. Louis, Mo., USA). Methoxy-poly(ethylene glycol)-amine powder (PEG-NH$_2$) was obtained from Jenkem Technologies (Beijing, PRC) and 4-(4,6-dimethoxy-1,3,5-triazin-2-yl)-4-methyl-morpholinium chloride (DMTMM) was from TCI America (Portland, Oreg., USA). All chemicals were used as received unless otherwise specified.

Equipment:

$M_n$ and polydispersity indices (PDI) for pAA were obtained using a Waters gel permeation chromatography (GPC) system equipped with two Ultrahydrogel™ columns (Waters) in series (500 Å and 250 Å), 1515 isocratic HPLC pump and 2414 refractive index detector with the temperature controlled at 30° C. The mobile phase employed was phosphate buffered saline (pH 7.4; PBS) at a rate of 0.8 ml min$^{-1}$ calibrated with poly(methacrylic acid), sodium salt standards. $^1$H NMR of pAA was performed using an Inova 400 MHz spectrometer with deuterium oxide (D$_2$O) as the solvent. Resonances were referenced to HOD at 4.81 ppm.

Example 1

Synthesis and Characterization of Polyacrylic Acid Backbone (pAA)

Methods:

Polyacrylic acid was synthesized by RAFT polymerization as described [Pelet et al. (2012) Macromol. Chem. Phys. 213:2536-40] using acrylic acid (AA), A-CPA as initiator (I) and CPA-DB as chain transfer agent (CTA) under anhydrous, airtight and dark conditions (FIG. 1A). To scale up, the general reaction conditions were as follows: AA (0.95 ml, 13.8 mmol) was added to a flame dried 5 ml brown ampule with one flea magnet, to which CPA-DB (5.3 mg, 19×10$^{-3}$ mmol) dissolved in 2.9 ml of nitrogen-purged methanol was added, followed by A-CPA (1.3 mg, 4.63×10$^{-3}$ mmol) dissolved in 0.7 ml of nitrogen-purged methanol. Nitrogen gas was bubbled through the reaction mixture for several minutes after addition of each reagent to prevent oxygen gas influx. After the last nitrogen purge, the reaction ampule was flamed sealed, placed in a 60° C. oil bath to initiate polymerization and allowed to stir for 48 hours. Upon reaction completion, the ampule neck was broken to expose the reactants to air and the solution was cooled in ice to stop polymerization. The solution was diluted with 0.01 M NaOH, dialyzed against deionized water for 3 days, with water changes twice daily, and then lyophilized to obtain a white, waxy powder. Characterization: $^1$H NMR (NOVA 400 MHz, D$_2$O, ppm): δ1.5-2.0 (pAA-CH$_2$—), δ 2.25-2.75 (pAA-CH—).

Results and Discussion:

The reaction scale was linearly increased ~1.6 fold over that previously reported [Pelet (20120)] to allow an initial analysis of potential challenges during scale-up for product manufacture. In general, the total reaction volume (4.6 mL) was maintained constant for each reaction shown in Table 1, while the mole ratios of the AA, I and CTA were varied to give different pAA backbone lengths. The [I]:[CTA] ratios were maintained constant at 0.25 while the [AA]:[CTA] ratios were varied to achieve the indicated molecular weights. Several batches of pAA were synthesized for each theoretical $M_n$, and if the experimental $M_n$ was within 5% error of the desired theoretical $M_n$, the reactions were considered acceptable. In general, pAA generated using the ratios from Table 1 always had the same $M_n$ within experimental error.

To achieve molecular weights greater than $M_n$ 100,000 with acceptable PDIs (preferably ≤1.35), AA concentrations greater than 3 M were required to avoid deviation from the theoretical $M_n$. To achieve even higher molecular weights ($M_n$ 200,000 or greater) with narrow PDI's, even higher monomer concentrations along with modified reaction conditions may be necessary.

For Table 1, the RAFT polymerization of AA was conducted in methanol @ 60° C. while maintaining [I]:[CTA] at 0.25 under airtight, oxygen-free conditions and varying [AA] and [AA]:[CTA]. This table provides the theoretical and sample experimental $M_n$ values as well as the PDI for the indicated pAA polymer. Experimental $M_n$ and PDI values were determined by GPC.

TABLE 1

Molecular weights of synthesized pAA

| Concentration of AA (M) | [AA]:[CTA] | Theoretical $M_n$ (g/mol) | Experimental $M_n$ (g/mol) | Polydispersity (PDI) |
|---|---|---|---|---|
| 3 | 762 | 60,000 | 61,700 | 1.34 |
| 5 | 1259 | 105,000 | 104,200 | 1.31 |
| 8 | 2509 | 145,000 | 145,600 | 1.28 |

Example 2

Synthesis and Characterization of pAA-g-PEG Polymer Brushes

Methods:

The pAA-graft-PEG copolymer (pAA-g-PEG) was synthesized by polymer analogous conjugation of monoaminefunctionalized PEG to the pAA backbone using DMTMM as the coupling agent based on the procedure of [Pelet et al. (2011) Bioconj. Chem. 22:329-37] and is shown schematically in FIG. 1B. The general reaction was as follows: 107,600 $M_n$ pAA (10 mg, 139 mmol of AA) and 2000 $M_n$ PEG-amine (610 mg, 305 mmol of PEG) were dissolved by stirring in 0.1 M borate buffer (3 ml, pH 8.5) in a 10 ml flask with magnetic stir bar. DMTMM (79 mg, 285 mmol) dissolved in 0.1 M borate buffer (0.6 ml) was added dropwise to the solution and the pH adjusted to 6-7 using 1 N HCl. The reaction volumes were fixed based on the concentration of pAA being maintained at ~3.3 g/L, provided the corresponding molar ratios of PEG would dissolve at the corresponding volumes. Otherwise reaction volumes were fixed based on maintaining PEG concentrations at 185 g/L (since dissolving a high mass of large $M_n$ PEG at certain molar ratios relative to AA monomers was difficult). Each conjugation reaction was conducted for 24 hours at room temperature, dialyzed against deionized water for 3 days and lyophilized to obtain a white powder. The nomenclature for the polymer brushes are given as pAA(a)-gr-PEG(b), where a and b are molecular weights of pAA and PEG respectively, and gr is the grafting ratio defined by the moles of PEG grafted to the pAA backbone divided by the moles of AA monomers in the pAA backbone.

To determine the hydrodynamic diameter of the polymers, dynamic light scattering (DLS) was used with pAA-g-PEG in aqueous solution. Each pAA-g-PEG was dissolved in filtered PBS at a concentration of 3 g/l and its hydrodynamic diameter measured using a Malvern Zetasizer ZS at 20° C. and a detector angle of 173 degrees. The light scattering intensity was measured as a function of time to correlate the Brownian motion of the polymer with hydrodynamic diameters calculated from the Malvern Dispersion Technology software supplied by the instrument manufacturer.

FTIR was used to determine the percent (%) conjugation of PEG onto pAA. Briefly, a standard curve was produced by varying mass ratios of pAA and PEG polymers dissolved in methanol (0.5-1% w/v). The polymer solutions were deposited as thin films on calcium fluoride ($CaF_2$) crystals and spectra recorded through DGS-TEC absorbance from 350-4000 $cm^{-1}$. A total of 64 scans were collected per sample. Single value decomposition (SVD) of each spectra was performed in Matlab and the component spectra of the SVD were transformed with a transformation matrix to fit the spectra of pure pAA and PEG respectively. The pAA coefficient fraction was calculated from the ratio of the fitted components and correlated to the mass percent to give the percent conjugation of PEG for each brush polymer.

Results and Discussion:

PEG-$NH_2$ was conjugated to the pAA backbone using the condensing agent DMTMM to activate the carboxylic acid groups on the pAA and create a stable amide linkage between the pAA and PEG. The brush polymer product is a statistical graft copolymer of pAA and PEG (pAA-g-PEG), composed of carboxylic acids and amide linked PEG side chains (FIG. 1B). As shown in Table 2, polymers with different ratios of [PEG]:[AA] were made, using a constant 1:1 mole ratio of [DMTMM]:[PEG] for each combination of pAA and PEG. During the conjugation reactions the solution would occasionally turn yellow, indicating cleavage of the thiocarbonylthio end groups of the pAA backbone to expose a free thiol group. The exposed thiol group functionalizes the end of the pAA-g-PEG polymer brushes, allowing the polymer brush to bind substrates, such as gold or other thiol or maleimide functionalized compounds or surfaces. The two-step method of graft copolymer brush synthesis was chosen to give tight control over the backbone length (by RAFT polymerization) and the percent graft substitution to eliminate problems associated with direct copolymerization, such as differences in monomer reactivity ratios.

Figure 2:
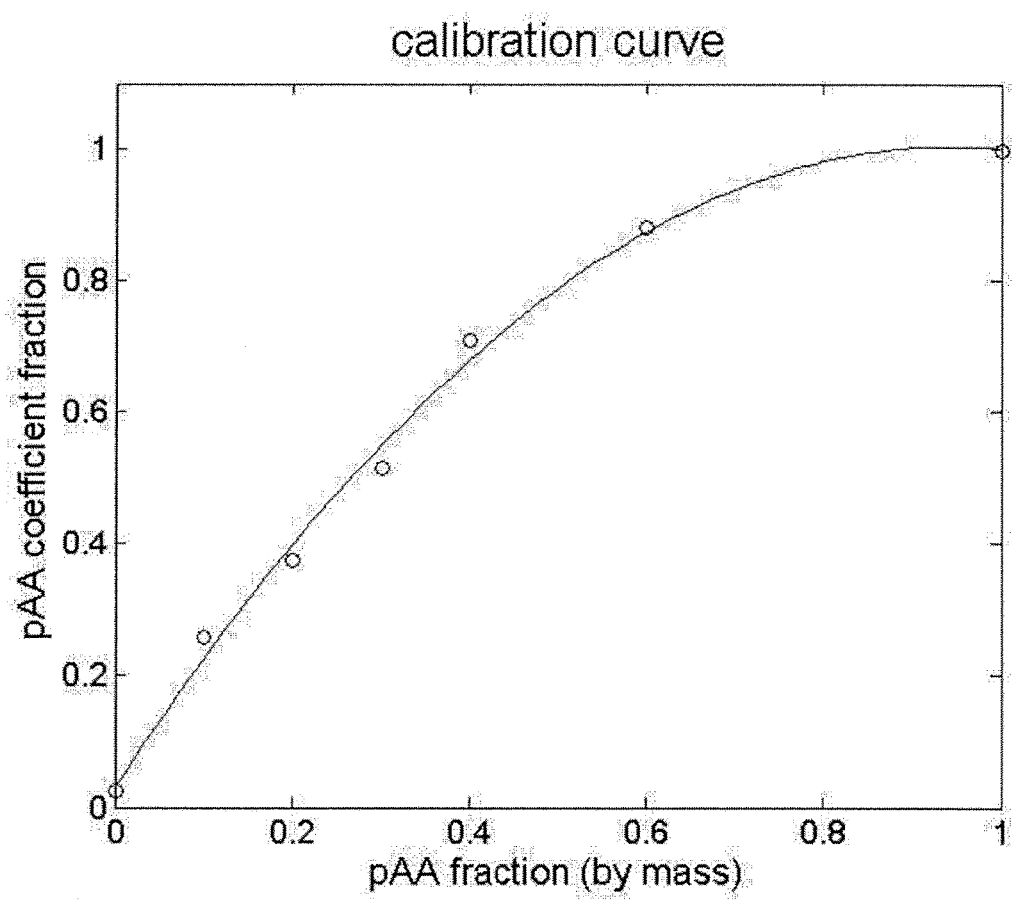
FIG. 2 shows a sample FTIR calibration curve for 105,000 g/mol pAA and 5000 g/mol PEG mixtures used for calculating the percent of grafted PEG on pAA-g-PEG. For each calibration curve, mass ratios varied from 1:9 to 6:4 of pAA:PEG. Pure pAA and PEG were also included. Data was fitted with quadratic equation with $R^2>0.99$.

Due to the high molecular weight and brush architecture of the pAA-g-PEG polymers, neither direct (e.g., DLS) nor indirect (e.g., GPC) measurement of PEG conjugation in the final copolymers was possible. Additionally, molecular weight calculation from $^1$H NMR end group analysis was not possible due to the overwhelming PEG peaks. This inability to characterize the molecular weight of polymer brushes is common so studies often report only the feed concentrations of reactants to distinguish between polymers [Mu et al. (2003) Tribology Lett. 15:395-405; Schmolke et al. (2011) Phys. Status Solidi A 208:1290-300]. Hence, a new method was developed using the infrared spectrum (IR) of each polymer to measure the degree of PEG conjugation to the pAA backbone, thereby allowing accurate calculation of the final copolymer molecular weights. Briefly, calibration curves correlating the percentage of pAA and PEG from unconjugated physical mixtures were generated from the respective IR absorbance spectrum for each combination of pAA and PEG molecular weights (see example in FIG. 2). The pAA coefficient fraction of each pAA-g-PEG was correlated to the calibration curves, thereby providing the pAA mass fraction of the sample which was then used to calculate the percent conjugation and calculated molecular weight of the pAA-g-PEG polymers (Table 2). From the data, higher grafting feed ratios lead to higher percent conjugation of PEG side chains. A comparison of higher to lower molecular weight PEG at the same grafting feed ratios generally shows lower percent conjugation yields for the higher molecular weight PEG, likely from the steric effects of the longer chains.

TABLE 2

Table of pAA-g-PEG polymer brushes

| Copolymer | $M_n$ pAA backbone (g/mol) | MW PEG side chain (g/mol) | (PEG:AA) grafting ratios | Percent conjugation (%) | hydrodynamic diameter (nm) |
|---|---|---|---|---|---|
| pAA(145)-2-PEG(10) | 145,000 | 10,000 | 2 | 16.1 | 110.5 |
| pAA(145)-2-PEG(2) | 145,000 | 2,000 | 2 | 32 | 84 |
| pAA(105)-1-PEG(5) | 105,000 | 5,000 | 1 | 41 | 103 |
| pAA(60)-2-PEG(10) | 60,000 | 10,000 | 2 | 9 | 91 |
| pAA(60)-2-PEG(5) | 60,000 | 5,000 | 2 | 30.5 | 69 |
| pAA(60)-0.5-PEG(5) | 60,000 | 5,000 | 0.5 | 4.7 | 64 |

In Table 2, above, the $M_n$ pAA is the theoretical Mn from Table 1). For the PEG:AA grafting ratios, [PEG]:[AA] varied while [PEG]: [DMTMM] was held constant at a 1:1 ratio.

Example 3

Boundary Lubrication of pAA-g-PEG Against Bovine Cartilage

Methods:

Frictional testing was conducted using a custom tribometer designed specifically for cartilage lubrication [Gleghorn et al. (2008) J. Biomech. 41:1910-8]. Using a Varian thermal bell jar evaporator, a 100 nm layer of chrome was deposited on a glass slide followed by a 200 nm gold coating. A 3 mg/ml solution of pAA-g-PEG in PBS was incubated on the gold coated slides for 1-3 days, to form self-assembling monolayers from thiol-gold interactions [Lowe et al. (2002) J. Am. Chem. Soc. 124:11562-3]. Atomic force microscopy (AFM) using a Digital Instruments' Dimension 3100 Atomic Force Microscope was conducted on pAA-g-PEG treated slides in contact mode under semi-hydrated conditions in PBS to observe coverage.

Figure 3:
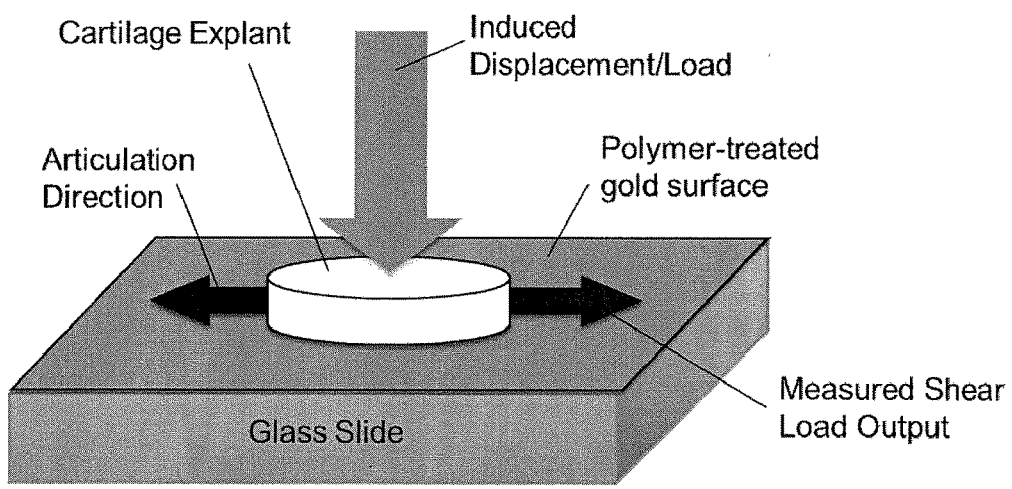
FIG. 3A provides a schematic diagram of a tribometer used for frictional testing of pAA-g-PEGs. A normal load is induced on the cartilage explant onto the polymer-treated gold coated glass. The coefficient of friction is determined by dividing shear load over normal load.
FIG. 3B is a cartoon of the brush copolymers tethered to gold-coated surfaces through the thiol group end-terminus of the pAA backbone.
Figure 3:
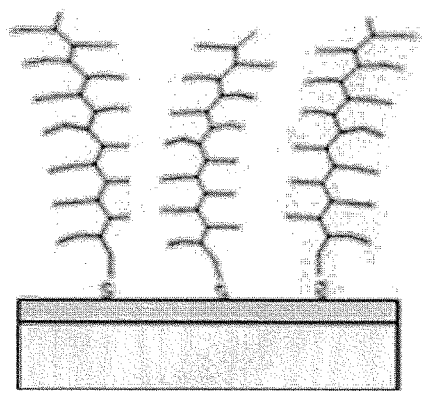

A six mm diameter cartilage explant was isolated from the patellofemoral grooves of 1-3 day old bovine calves, and denuded in 1.5 M saline solution to strip cartilage of native lubricin. The polymer-treated slides and denuded cartilage explants were evaluated on the tribometer in the presence of PBS to determine coefficient of friction under boundary mode conditions as shown in FIG. 3. For example, a normal load was induced from the cartilage explant onto the polymer-treated gold coated glass and the polymer-treated sample was then articulated perpendicular to the normal load for 4 cycles. To create boundary mode lubrication conditions, shear articulation speeds of 0.3 mm/sec and 40% compressive strain were used [Gleghorn (2008)]. The resulting shear load was recorded and the coefficient of friction determined by dividing shear load over normal load.

A gold-coated slide without polymer was used as a negative control and LUB:1 was used as a control.

Results and Discussion:

Gold-coated slides incubated with pAA-g-PEG brushes were investigated by AFM to give a visual qualitative analysis of polymer surface coverage. The images obtained were representative of the pAA-g-PEG coverage on the gold surfaces. In general, the polymer brushes formed aggregates spread uniformly over the surface, with occasional small clusters observed.

Figure 4:
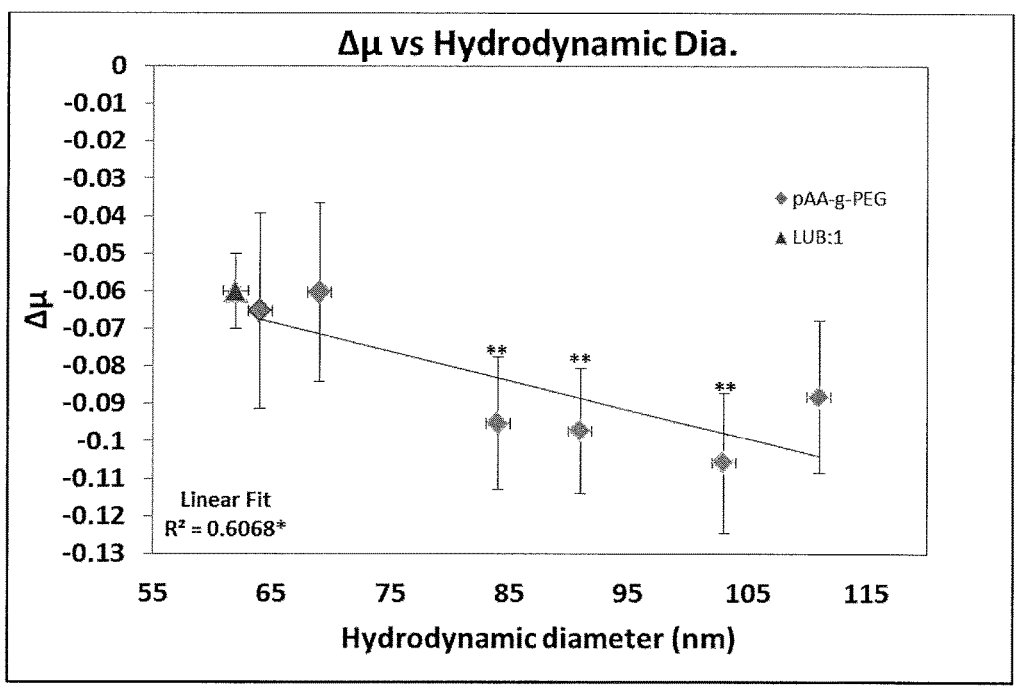
FIG. 4 depicts the boundary lubrication results of polymer-treated slides. Specifically, the graph shows the change in coefficient of friction ($\Delta\mu$) relative to a negative control (untreated slides) plotted against hydrodynamic diameter. Each pAA-g-PEG data point is the average of 5 samples. LUB:1 served as a control.

The quantitative results for the boundary mode lubrication of the polymers against bovine articular cartilage are given in Table 3 and shown graphically in FIG. 4. Results are given as change in coefficient of friction (AO compared to negative control (untreated slides). Each pAA-g-PEG data point is the average of 5 samples. Linear fit has $R^2>0.6$ and shows a significant trend (*$p<0.05$, one tailed t-test). pAA(60)-2-PEG(10), pAA(105)-1-PEG(5), and pAA(145)-2-PEG(2) show a significant difference compared to LUB:1 (**$p<0.05$, one tailed t-test); while the remainder had comparable $\Delta\mu$.

In FIG. 4, the results are plotted by increasing copolymer hydrodynamic size with LUB:1 as a comparison [Gleghorn et al. (2009) J. Orthop. Res. 27:771-7]. For these frictional tests, slow articulation speeds (0.3 mm/sec), as well as high compressive strain (40%), were employed to mimic boundary mode lubrication for each test. Here compressive strain is measured over compressive forces to allow more uniform tests on multiple cartilage explants.

All of the pAA-g-PEG's exhibited a decrease in $\Delta\mu$ compared to the untreated control surface. The data shows a significant trend correlating increasing hydrodynamic size and decreasing $\Delta\mu$ of the pAA-g-PEG's (FIG. 4). Comparing these results to the LUB:1 positive control, the $\Delta\mu$ induced by each pAA-g-PEG brush copolymers is comparable or significantly superior in the case of pAA(60)-2-PEG(10), pAA(105)-1-PEG(5), and pAA(145)-2-PEG(2). The coefficient of friction decreases significantly for the polymers with >80 nm hydrodynamic diameter excluding the pAA(145)-1-PEG(10). This is interesting since LUB:1 was shown in previous in vivo rat models to be an effective preventative of cartilage damage and inhibited OA disease progression [Flannery (2009)]. Based on these preliminary in vitro studies on ex vivo bovine cartilage explants, pAA-g-PEG's appear as effective or more effective than LUB:1 at lubricating cartilage surfaces and have the potential to inhibit OA disease progression.

TABLE 3

Frictional testing of polymer-treated gold coated slides

| Polymer | Hydrodynamic diameter (nm) | $\Delta\mu \pm$ SEM |
|---|---|---|
| None | N/A | $0.0000 \pm 0.0423$ |
| LUB:1 | 62 | $-0.0600 \pm 0.01$ |
| pAA(60)-0.5-PEG(5) | 64 | $-0.0653 \pm 0.0579$ |
| pAA(60)-2-PEG(5) | 69 | $-0.0603 \pm 0.0581$ |
| pAA(145)-2-PEG(2) | 84 | $-0.0952 + 0.0397$ |
| pAA(60)-2-PEG(10) | 91 | $-0.0972 \pm 0.0375$ |
| pAA(105)-1-PEG(5) | 103 | $-0.1058 \pm 0.0417$ |
| pAA(145)-1-PEG(10) | 110.5 | $-0.0882 \pm 0.0457$ |

In Table 3 above, SEM is Standard Error of the Mean. Recombinant lubricin (LUB:1) results are from previous study [Gleghorn (2009)].

Example 4

Functionalized End Groups

Previous work established that the cartilage binding domain of lubricin is located at the carboxy terminus or near a hemopexin-like amino acid sequence [Jones et al. (2007) J. Ortho. Res. 25:283-922]). A series of peptide sequences previously identified to bind to cartilage are evaluated to quantify how they influence boundary mode lubrication of the biomimetics. Examples of these peptides are shown in Table 4. Additionally, these brush polymer peptide conjugates are investigated to determine how their binding kinetics ($k_b$), binding constants ($K_D$) and target cartilage binding protein influence boundary mode lubrication.

TABLE 4

Cartilage Binding Sequences

| Peptide sequence | Binding domain | Reference(s) |
|---|---|---|
| TKKTLRT (SEQ ID NO: 1) | Collagen | de Souza et al. (1992) J. Biol. Chem. 267: 13763-13767. |
| SQNPVQP (SEQ ID NO: 2) | Collagen | Rothenfluh et al. (2008) Nature Mat. 7: 248-254. |
| WYRGRL (SEQ ID NO: 3) | collagen | Rothenfluh et al. (2008) Nature Mat. 7: 248-254. |
| SYIRIADTN (SEQ ID NO: 4) | Collagen | Paderi et al. (2009) Tissue Eng. 15: 2991-2999; Weber et al. (1996) J. Biol. Chem. 271: 31767-31770. |
| CQDSETRFY (SEQ ID NO: 5) | Fibronectin | Sistiabudi et al (2008) Langmuir 24: 1591-1594; Sistiabudi et al. (2009) Biotechnol. Bioeng. 102: 1723-1729. |

The peptides listed in Table 4 were selected to balance their established cartilage binding characteristics with a reasonable amino acid length.

The peptides are synthesized by standard peptide chemistry, N-terminally labeled with maleimide and conjugated to the thiol end-group of the pAA-g-PEG polymers using a thiol-maleimide reaction with 2× excess of the free thio group. The degree of conjugation is determined using Ellman's reagent and the peptide conjugation confirmed and quantified by amino acid analysis. Unconjugated peptide is removed by dialysis and unconjugated brush copolymer, if any, is will be removed by SulfoLink Immobilization resin (Pierce). Peptide-bound brush polymers are evaluated for boundary mode lubricity as described in Example 3 and for in vivo activity as described in Example 5.

Example 5

Rat ACL Transection Model for Osteoarthritis

The ACL transection model in rats is an accepted osteoarthritic model for evaluating efficacy of OA treatments. The model has been used to quantify cartilage degeneration prevention and chondroprotection of full-length lubricin isolated from human synoviocytes grown in culture, truncated recombinant lubricin and synovial fluid isolate from joint replacement patients [Jay et al. (2010) Arthritis Rheum. 62:2382-91] and was used to establish and quantify the efficacy of the 60K-2K-50% brush copolymer. The results showed that this polymer prevented the progression of cartilage degeneration. Notably, the 60K-2K-50% polymer prevented changes in cartilage, bone and meniscus, functionally manifest in lower tissue roughness and friction coefficient.

Methods:

Eight to ten week-old male Sprague-Dawley rats were randomly and blindly assigned to each treatment group (N=12 rats/group). Each rat leg was randomly assigned to a treatment or control group (one treatment, one control for each rat) so that each rat is its own control.

Rats were anesthetized by intraperitoneal injection with ketamine-xylazine cocktail and a midline skin incision (tibial tubercle to superior pole of patella) in antiseptic-prepared skin followed by a medial parapatelar arthrotomy (tibial tubercle to quadriceps, leaving 1 mm patellar ligament medially) was performed. Following patellar luxation, the retropatellar fat pad was removed and the anterior cruciate ligament (ACL) identified in the intercondylar notch and the ligament transected at the tibial attachment. The knee was extended, patella reduced, and Lachman's test (i.e., anterior tibial translation) used to establish anterior instability. The procedure was completed by closure of both the arthrotomy and skin with 4-0 Vycril interrupted suture.

The 60K-2K-50% brush copolymer, pre-sterilized by treatment with 70% ethanol and sterile dried under vacuum, was dissolved in sterile-filtered PBS (0.2 μm filter) to a final volume of 150 μl at a concentration of 3 mg/mL. Filtration sterilization of the polymer directly prior to administration is not possible owing to the very high molecular weights of the brush copolymers (i.e., the polymers are too large to pass through a sterilization filter), and the sterile preparation method adopted for this work resulted in a 0% infection rate for the 60K-2K-50% studies. Anesthetized rat are injected with polymer solutions and PBS controls (50 μl) through the center of the patellar ligament (3 mm depth) with the knee at 90 degrees flexion.

The rats were sacrificed (isoflurane, 33% by inhalation) and joints from six rats were examined for histological differences, biochemical differences and for residual polymer content. The joints from remaining six rats were mechanically evaluated by tribometry and profilometry.

Figure 5:
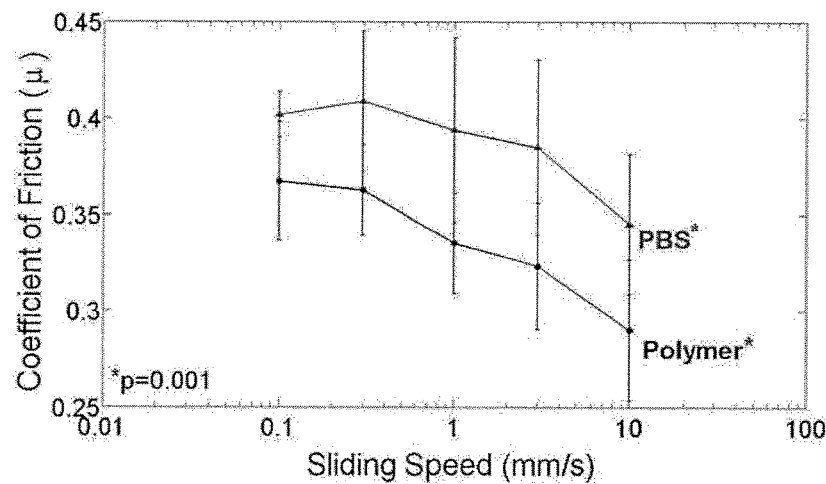
FIG. 5 graphically displays the coefficient of friction ($\mu$) of the pAA-g-PEG brush polymer designated as 60K-2K-50% (treated) and PBS (untreated) on tibial cartilage explants as a function of sliding speed. The results show a statistically significant (p=0.001) difference between groups at each speed (ANOVA analysis).

Results and Discussion:

For mechanical evaluation, three mm cartilage samples were removed from the tibial plateau, one each from the medial and lateral compartments. Samples were loaded into the tribometer to determine frictional behavior as generally described in Example 3. The lubrication results from the 60K-2K-50% in vivo evaluation are shown in FIG. 5 and data points represent the average values obtained from the two sites.

Figure 6:
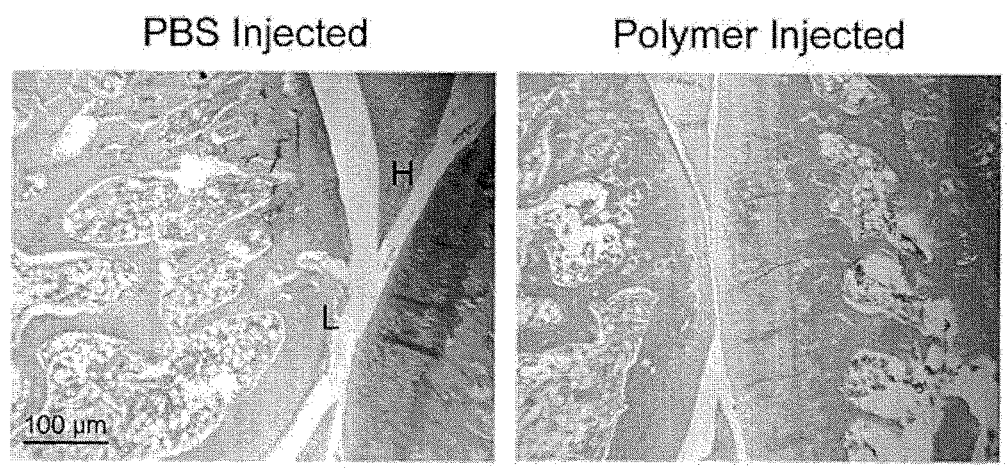
FIG. 6 Safranin-O stained histology section of knee joints from ACL transected untreated rat knees (PBS injection) and ACL-transected, treated rat knees (60K-2K-50% injection) showing lesions (L) and hypertrophy (H) in the PBS samples but not in the polymer treated samples.

For histological evaluation, isolated knee samples were decalcified, paraffin embedded and coronal sections obtained. Various regions were sectioned with a cryo-microtome (250 μm per section) to acquire sections containing femoral condyles, tibial plateaus as well as menisci. Sections were stained with Safranin-O to visualize sGAG content and with hematoxylin and eosin (H&E) to visualize cell and matrix architecture (FIG. 6), showing the presence of articular cartilage lesions (L), associated subchondral bone remodeling, and focal regions of hypertrophy and cloning in the meniscus (H) in the PBS samples and no changes in the articular cartilage, bone, or meniscus morphology in the 60K-2K-50% samples. The histological results compare favorably to the recombinant lubricin (LUB:1) as well as full length lubricin. The OARSI-modified Mankin score was used to measure and score cartilage degeneration for each joint surface by at least three blinded and histology-trained individuals per section [Pritzker et al. (2006) Osteoarthritis Cartilage 14:13-29].

Figure 7:
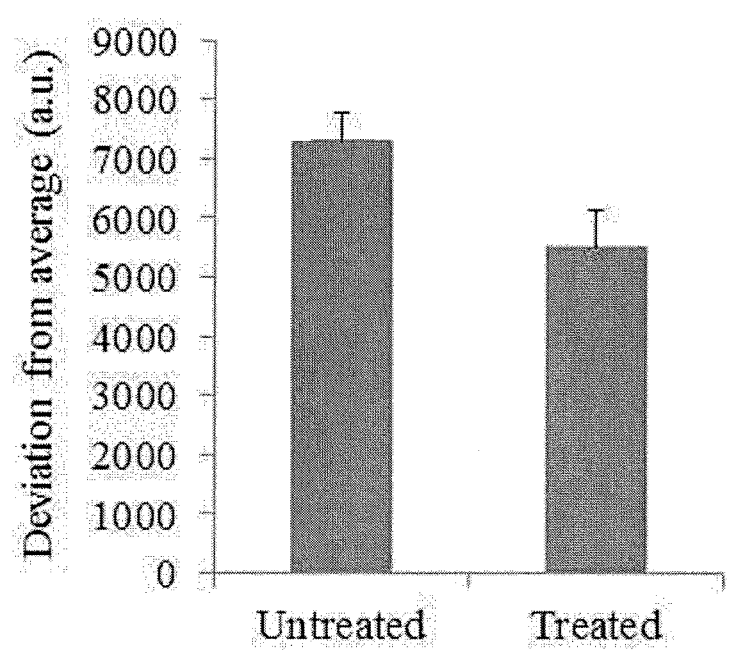
FIG. 7 is a bar graph depicting the surface roughness of explanted cartilage from ACL-transected, untreated rat knees (PBS injection) and ACL-transected, treated rat knees (60K-2K-50%) and shows statistically significant differences between groups (p<0.01).

Surface roughness of the cartilage was evaluated by profilometry. Each cartilage explant was imaged on an ADE Phase Shift MicroXAM optical interferometric profiler and height measurements taken over three different 849 μm×631 μm scans. Histograms of the measured heights at each pixel of the scanned image were made and converted to bar graphs to allow facile identification of differences (FIG. 7). The results shows statistically significant differences between untreated and treated groups (p<0.01).

Biochemical analysis of the tissues is used to quantify cell and tissue integrity. Specifically, the concentrations of proteoglycan and collagen, as well as cell density, are measured. Tissue samples are weighed (wet weight), lyophilized to dryness, weighed (dry weight) and digested in papain (1.25 mg/ml) at 60° C. for 16 hrs. Digests are analyzed for sulfated proteoglycans using the dimethylmethylene blue dye binding assay [Farndale et al. (1982) Connect Tissue Res. 9:247-248], for collagen using the hydroxyproline assay using diaminobenzaldehyde [Neuman et al. (1950) J. Biol. Chem. 184:299] and for DNA content by Hoechst dye 33258 staining [Kim et al. (1988) Anal. Biochem. 174:168].

Residual polymer is identified by immunostaining using rabbit antiPEG-specific antibodies incubated with cartilage sections, followed by incubation with biotinylated anti-rabbit antibodies.

We claim:

1. A graft brush polymer comprising (i) a polyacrylic (PAA) backbone having a polydispersity index ranging from 1.0 to about 1.5 and a molecular weight of about 60 kDa, (ii) polyethylene glycol (PEG) brush segments having a molecular weight of about 2 kDa, and (iii) at least one functionalizable group, selected from thiol and amine groups, located on at least one of the two terminal ends of the PAA backbone, wherein said graft brush polymer has a PEG:AA grafting ratio of about 2, wherein the grafting ratio is defined as the moles of PEG grafted to the PAA backbone divided by the moles of acrylic acid (AA) monomers in the PAA backbone.

2. The polymer of claim 1, wherein said functionalizable terminal group is a thiol group.

3. The polymer of claim 2, wherein a cartilage binding domain is attached to said polymer via said thiol group.

4. The polymer of claim 3, wherein said cartilage binding domain is a peptide moiety selected from the group consisting of TKKTLRT (SEQ ID NO: 1), SQNPVQP (SEQ ID NO: 2), WYRGRL (SEQ ID NO: 3), SYIRIADTN (SEQ ID NO: 4) and CQDSETRFY (SEQ ID NO: 5).

5. The polymer of claim 1, wherein said graft brush copolymer further comprises at least one binding agent that can bind the graft brush copolymer to a biological tissue.

6. The polymer of claim 5, wherein said binding agent is a hydrophobic alkane chain or a sterol.

7. A pharmaceutical composition comprising the graft brush copolymer of claim 1 and a pharmaceutically-acceptable carrier.

\* \* \* \* \*